United States Patent [19]

Lin et al.

[11] Patent Number: 5,250,029
[45] Date of Patent: Oct. 5, 1993

[54] ZERO-RESIDUAL ZERO-TIP BALLOON CATHETER

[76] Inventors: Edward Lin, 556 Roxbury Dr. NW., Massillon, Ohio 44646-3281; Wallace Lin, 926 Mesa Oak Ct., Sunnyvale, Calif. 94086-8224

[21] Appl. No.: 966,617

[22] Filed: Oct. 26, 1992

Related U.S. Application Data

[63] Continuation of Ser. No. 788,588, Nov. 6, 1991, abandoned.

[51] Int. Cl.$^5$ ............................................. A61M 29/00
[52] U.S. Cl. ...................................... 604/96; 606/192
[58] Field of Search ............................... 604/96–103, 604/53; 606/192–194

[56] References Cited

U.S. PATENT DOCUMENTS

| | | | |
|---|---|---|---|
| 3,438,375 | 4/1969 | Ericson | 604/96 |
| 3,811,448 | 5/1974 | Morton | 604/96 X |
| 3,954,110 | 5/1976 | Hutchison | 604/96 X |
| 4,022,216 | 5/1977 | Stevens | 604/96 X |
| 4,284,081 | 8/1981 | Kasper et al. | 604/96 |
| 4,295,464 | 10/1981 | Shihata | 604/96 X |
| 4,351,342 | 9/1982 | Wiita et al. | 604/96 |
| 4,575,371 | 3/1986 | Nordquist et al. | 604/100 X |
| 4,958,634 | 9/1990 | Jang | 606/194 |
| 5,116,305 | 5/1992 | Milder et al. | 604/96 X |

Primary Examiner—John D. Yasko
Attorney, Agent, or Firm—Renner, Kenner, Greive, Bobak, Taylor & Weber

[57] ABSTRACT

A balloon type catheter used for drainage or irrigation and drainage of a body cavity such as the bladder having a tapered tip with a large elongated lateral opening spanning the approximate distance of the balloon so as to allow complete and maximally effective drainage from the most dependant portion of said body cavity. An inflatable balloon partially surrounds the catheter's distal end, and circumscribingly ending at the lateral borders of the large drainage opening. When the balloon is inflated, the tip of the catheter becomes flush or recessed relative to the balloon thereby preventing the tip from abutting against delicate tissue as to cause compression injury. A gully in the balloon created by the elongated drainage opening act as a vent and buffer the delicate surrounding tissue from negative pressure injury. When used for irrigation and drainage, the catheter has an irrigation conduit that opens at the tip of the catheter to deliver fluid that flushes the cavity and the effluent is drained out via the aforesaid large lateral opening which is designed in this invention to position itself at the lowest portion of said body cavity.

26 Claims, 4 Drawing Sheets

ZERO-RESIDUAL ZERO-TIP BALLOON CATHETER

This is a continuation of application Ser. No. 788,588, filed Nov. 6,1991 now abandoned.

BACKGROUND OF THE INVENTION

1. Field of the Invention

This invention relates to balloon catheters, commonly used to drain a body cavity such as the bladder. In particular, this invention relates to novel designs of balloon catheter that enable it to overcome several major disadvantages and deficiencies in the prior art.

2. Description of Prior Art

Since the Foley type balloon catheter was invented in 1965, it has become the most widely used catheter in urology. Many patients require the assistance of such catheters for a myriad of reasons including incontinence, bladder outlet obstruction (such as from prostatic hypertrophy, stone or tumor), urethral stricture, trauma and post-surgical recovery. There are two major types of balloon catheters, the most common being the "two-way" Foley which has 2 channels and is used primarily for drainage, and the "three-way" Foley which has 3 channels and is used for irrigation and drainage. Both types of catheters have drainage openings situated distal to/above the balloon, just proximal to the catheter tip.

The most important function served by balloon catheters is the drainage of urine from the bladder. When the natural passage of urine from the bladder is impaired for whatever reason, the patient is at risk of developing a spectrum of complications including bladder and kidney infections, secondary septicemia, renal failure and even death.

Unfortunately, three factors associated with bladder catheterization further predispose the already compromised patient to such infections: First, the very act of catheterization risks introduction of pathogens into the urinary tract. Second, the incomplete drainage of the bladder resulting from using currently available catheters which have drainage openings situated above the balloon, encourages stagnation and promotes bacterial growth. And third, pressure against the bladder mucosa exerted by the catheter tip (causing "polyposis cysta/bladder callus/catheter tip necrosis"), or by negative pressure in the drainage tubing (causing hemorrhagic pseudopolyps), all lead to weakened local defenses against bacterial invasion and colonization. Millions of elderly and debilitated patients, including those suffering from progressive or traumatic neurologic disorders such as multiple sclerosis and paraplegia also chronically depend on indwelling catheters for bladder drainage. In addition to the aforementioned problems which can manifest even after a few days of catheter therapy, these patients are at high risk of developing bladder infections and bladder stone formation from chronic incomplete drainage of urine from the bladder. Because currently available catheters do not drain from the lowest portion of the bladder, renal casts, concretions and sediments settle and accumulate in the bladder neck leading to painful stone formation tha usually require surgical removal.

Even for short term use, the irritation caused by the catheter tip often leads to pain and bladder spasms. The protruding tip of the catheter is also a concern to the surgeon after bladder surgery since it may disrupt suture lines. Lastly, the histologic changes in the bladder mucosa induced by pressure from the catheter tip, or suction injury from negative pressure in the drainage tubing, can confuse diagnosis upon cystoscopy in that the inflamed area may need to be biopsied in order to rule out malignancy. The problems and complications described in the preceding paragraphs result in patient discomfort, morbidity and mortality that cost millions of dollars in added health care costs annually.

There is considerable prior art attempting to improve the design of the basic balloon catheter to overcome the aforementioned problems. Ericson in U.S. Pat. No. 3,438,375 (April 1969) disclosed several embodiments of catheters, the balloons of which either do not fully buffer the bladder mucosa from the catheter tips or when they do, come with blunt catheter tips that are difficult to insert. By nature of their shared inferior design, the Ericson catheters also have much narrower lumens which predispose them to early obstruction and failure.

Morton in U.S. Pat. No. 3,811,448 (May. 1974) disclosed a catheter with a conventional tip and drainage opening distal to an asymmetric one-sided balloon which when inflated will cause the catheter tip to bend and lower the distal opening, thus marginally improving bladder drainage. In addition, just below the lower border of the balloon is another drainage opening. This opening is situated too low to be consistently within bladder cavity to serve drainage function.

Hutchison in U.S. Pat. No. 3,954,110 (May. 1976) disclosed a "bilobated" balloon enclosing a reinforced catheter tip, said balloon is retracted inferiorly at two diametrically opposite points to expose two drainage openings. The balloon is designed to give early indication of the correct positioning of the catheter within the bladder and also intended to drain the bladder completely. However, the fully circumscribing balloon above the drainage openings in combination with the funnel-shaped bladder neck make it likely that as the bladder empties, its wall will collapse around the greatest transverse diameter of the balloon, shutting off the body of urine from the drainage openings and thus impede further drainage. The design of the blunt reinforced catheter tip also renders the catheter difficult to insert.

Stevens in U.S. Pat. No. 4,022,216 (May 1977) disclosed a balloon catheter that has its tip enclosed by a second, more distal balloon. The extra balloon increases the cost of manufacture and upon inflation, adds to the total length of the catheter in the bladder, limiting the degree of free collapse of the bladder and can indirectly cause the very type of pressure injury it was designed to avoid. Since the Stevens catheter has a conventional type drainage opening that is above the retention balloon it also cannot allow for complete drainage of the bladder.

Kasper et al. in U.S. Pat. No. 4,284,081 (August 1981) disclosed a doughnut shaped balloon mounted transversely at the distal end of a catheter, said balloon has a funnel-shaped drainage opening. While this design may allow slightly better, but still incomplete, drainage of the bladder, it creates a serious problem in the process. The outflaring distal orifice and the transversely positioned balloon make insertion difficult, requiring the use of a stylet which increases risk of trauma. Furthermore, the critical relationship between the radial boss on the stylet and the annular boss on the catheter is such that the catheter lumen must be considerably and disadvantageously narrowed by the annular boss in order to attain any reasonable degree of protection against accidental perforation of viscus by the stylet.

Wiita et al. in U.S. Pat. No. 4,351,342 (September, 1982) disclosed several embodiments of balloon catheters, the tips of each is completely encased by, and free floating (except for one three-way catheter embodiment) in, said balloon upon inflation. This free-floating tip design cannot ensure that the catheter tip will be buffered by the balloon, for the following reason: Tilting, angulating or thrusting of the catheter as can happen with any patient movement, may lead to catheter tip pushing right against the relatively untethered balloon wall, thus abrogating the very benefit such design is supposed to provide. Because the drainage opening in each of Wiita's catheter embodiments ends above the inferior border of its corresponding retention balloon, complete bladder drainage cannot be achieved by either his two-way or three-way designs. Also since each drainage opening is completely and circumscribingly surrounded by a balloon, not only would the catheter's manufacture be complicated by a high incidence of balloon failures, in clinical use, the contracting bladder wall during emptying will close upon this type of drainage orifice easier and sooner, leading to obstruction and incomplete emptying.

More recently, Nordqvist et al of Sweden disclosed in U.S. Pat. No. 4,575,371 (March 1986) a catheter with a unique tulip-shaped balloon which when inflated, projects distally to surround the tip of the catheter, much like flower petals shielding the pistil. The intended goal is to prevent the catheter tip from impinging against the bladder mucosa and to prevent negative-pressure suction injuries. The unusual balloon design, calling for a thicker wall proximally and angling against the direction of insertion would make both manufacture and its insertion difficult. The narrow funnel-shaped crevice between the catheter tip and the inflated balloon also promote sediment collection and encrustation leading to early obstruction. The Nordqvist balloon catheter also does not permit complete drainage of the bladder.

None of the aforediscussed prior art since Foley has enjoyed any commercial success, presumably due to the inherent drawbacks in their design. It is apparent from the preceding review of prior art, that a still unmet need exists for a balloon catheter that is simple and economical to manufacture, easy and comfortable to insert, prevents catheter tip irritation and mucosal suction injury, consistently and reliably achieve complete bladder drainage and allow for efficient and thorough irrigation. It is the object of the present invention to provide a novel, unique catheter possessing all of the above desirable characteristics.

LIST OF REFERENCE NUMERALS

Figure 1:
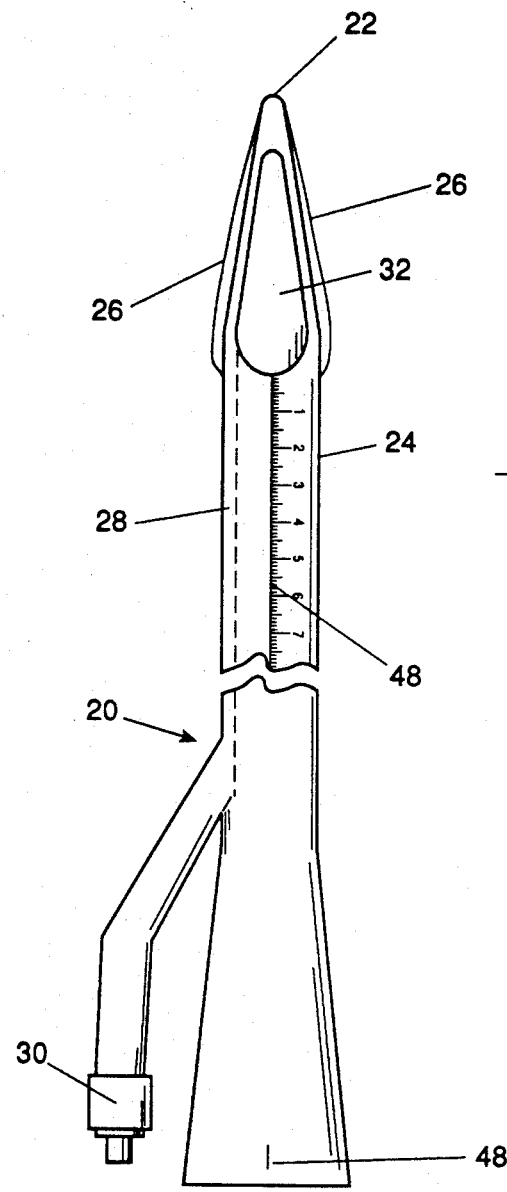
FIG. 1 shows a perspective view of an embodiment of the present invention in the form of a two-way balloon catheter.

20: two-way balloon catheter
22: tapered tip
24: catheter body
26: balloon
28: balloon inflation channel
30: balloon inflation valve
32: drainage opening
34: drainage lumen
36: bladder wall
38: irrigation inlet
40: irrigation channel
42: irrigation outlet
44: irrigation fluid
46: blood clot or stone
48: marker line for position of drainage opening.
50: three-way balloon catheter
52: Optional reinforcement.

DETAILED DESCRIPTION OF PREFERRED EMBODIMENTS

Referring now to FIG. 1 which shows a perspective view of the first embodiment of this invention in the form of a two-way balloon catheter 20. Catheter 20 has a tapered tip 22 at its distal end and a catheter body 24 spanning the tip to the proximal end. Connected right up to, and partially surrounding the tip of the catheter is an inflatable balloon 26 which is connected to a balloon inflation channel 28 running from the balloon cavity and ending at the balloon inflation valve 30. The balloon does not completely encircle the distal end of the catheter and stops at the longitudinal borders of a somewhat tear-drop shaped drainage opening 32. The width of opening 32 is almost the internal diameter of catheter body 24 so as to maximally ease drainage of particulate material such as clots or stones.

The catheter is optionally imprinted with one or more suitable visual marks such as one or more graduated longitudinal marker lines 48 which can be radiopaque and which are aligned with or opposite a fixed structure such as the drainage opening 32 and serve to indicate from the outside the orientation of the opening within the bladder. In addition, the measurement markings on the catheter provide useful measurement information such as the distance from bladder neck to urethral meatus, etc., thereby permitting instant recognition of whether or not a catheter so marked has slipped out of position.

Figure 2:
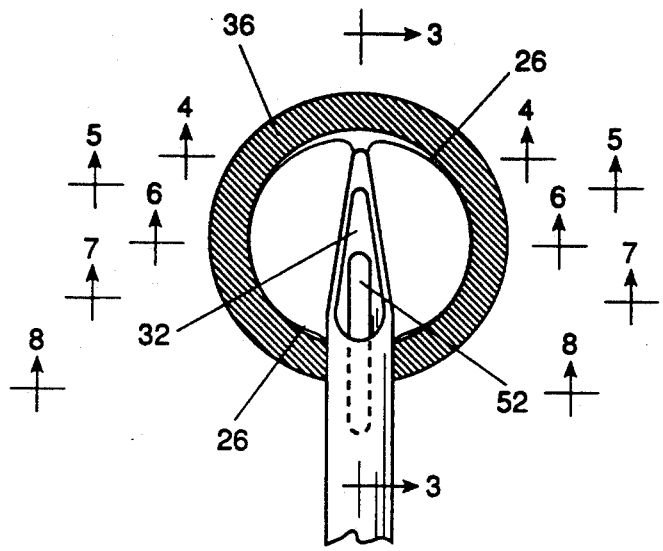
FIG. 2 shows the catheter in FIG. 1 with its balloon inflated within a bladder that is completely emptied and has contracted itself around the balloon.

FIG. 2 shows the catheter in FIG. 1 within a bladder cavity that has been emptied of urine and has assumed a contracted configuration around the balloon. After the catheter has been inserted into the bladder and the balloon inflated, the upper surface of the balloon rises above the catheter tip such that the catheter tip appears as the depression in the center of a dimple and therefore cannot cause pressure-type injury. This uniquely advantageous design can be achieved by bonding a small area of the balloon, approximately 2 to 4 square millimeters, overlying the tip of the catheter to the tip of the catheter itself. Or it can be obtained by deliberately positioning a small portion of the balloon beyond or distal to the catheter tip in the process of bonding the balloon to the catheter tip.

As illustrated, the large drainage opening 32 spans a larger than usual distance, ensuring that at least part of the opening will always be at the level of the bladder neck even if the catheter should be slightly displaced as can happen with patient movement. This second uniquely advantageous feature ensures the greatest likelihood of complete bladder drainage under all conceivable clinical conditions. Depending on the material used to make the catheter body, it may be advantageous to incorporate an optional polymer or metallic reinforcement 52 which compensates the possible weakening of the catheter wall by the large drainage opening 32.

Figure 3:
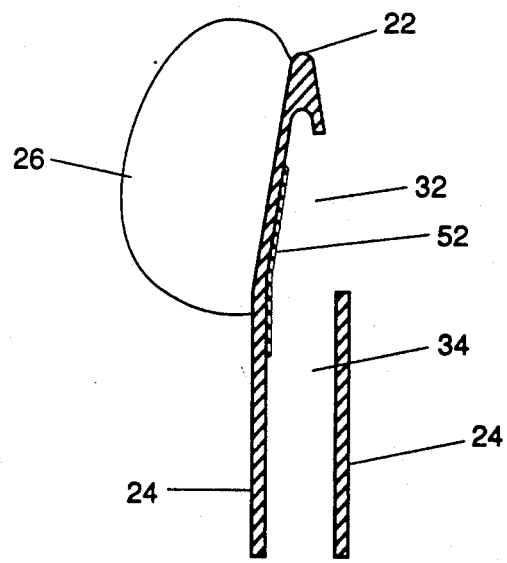
FIG. 3 is a cross sectional view taken along the line 3—3 in FIG. 2.
Figure 4:
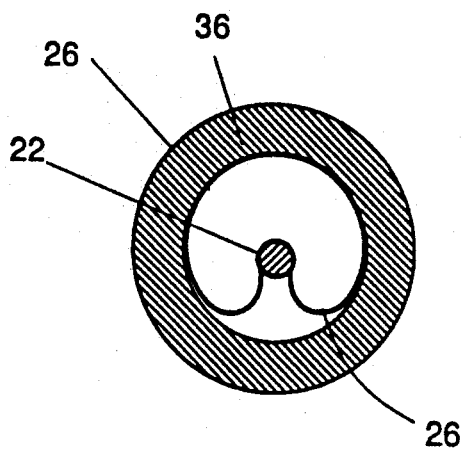
FIG. 4 is a cross sectional view taken along the line 4—4 in FIG. 2.
Figure 5:
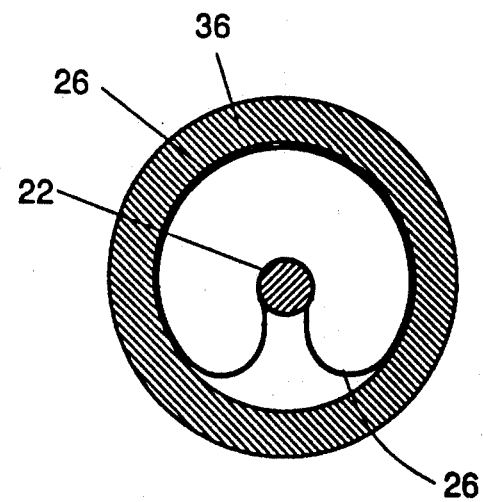
FIG. 5 is a cross sectional view taken along the line 5—5 in FIG. 2.
Figure 6:
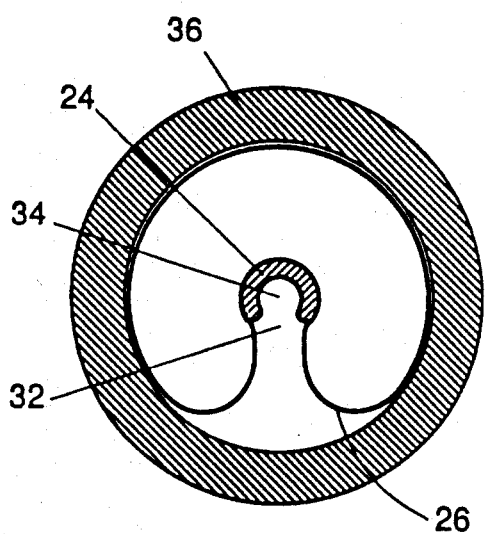
FIG. 6 is a cross sectional view taken along the line 6—6 in FIG. 2.
Figure 7:
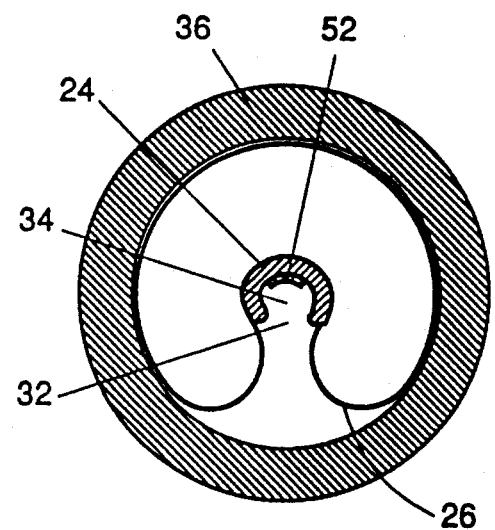
FIG. 7 is a cross sectional view taken along the line 7—7 in FIG. 2.

FIG. 3 is a cross sectional view taken along the line 3—3 in FIG. 1. The catheter tip 22 is substantially tapered and has a solid point to provide rigidity and ease the insertion of the catheter. In the unlikely circumstance the insertion is difficult even with such a tapered point, a stylet may be used safely since its tip would be securely covered within and by the concave interior of the catheter tip. Once again, the optional longitudinal reinforcement 52 is shown. It can be embedded in the catheter wall, providing a flush surface or be exteriorly attached with suitable bonding means.

FIGS. 4 through 8 show transverse cross sectional views of the catheter in FIG. 2 along their respective corresponding lines. As illustrated, the catheter tip is very tapered at its point and is solid in structure distally with an internally concave apex. Note also that the gap between the two borders of the balloon wall to either side of the tear-shaped drainage opening 32 progressively widens to maintain a gully from the top to the bottom of the balloon. As can be seen in FIGS. 4 through 7, this gully at all times provide an open channel for drainage of urine to the drainage opening even if the bladder wall 36 is completely collapsed and contracted around the balloon. Furthermore, the gully, serving as a vent, and in conjunction with the soft balloon wall on either side keeping bladder mucosa away from the drainage opening, prevents any negative-pressure injury from occurring. This is the third important advantage not provided by prior art.

Figure 8:
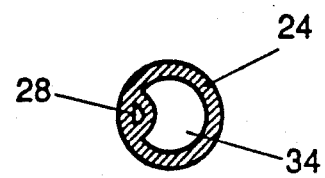
FIG. 8 is a cross sectional view taken along the line 8—8 in FIG. 2.

FIG. 8 shows a cross sectional view of the catheter body 24 taken along line 8—8 in FIG. 2 showing the lumen divided into a main drainage channel 34 and a small balloon inflation channel 28.

Figure 9:
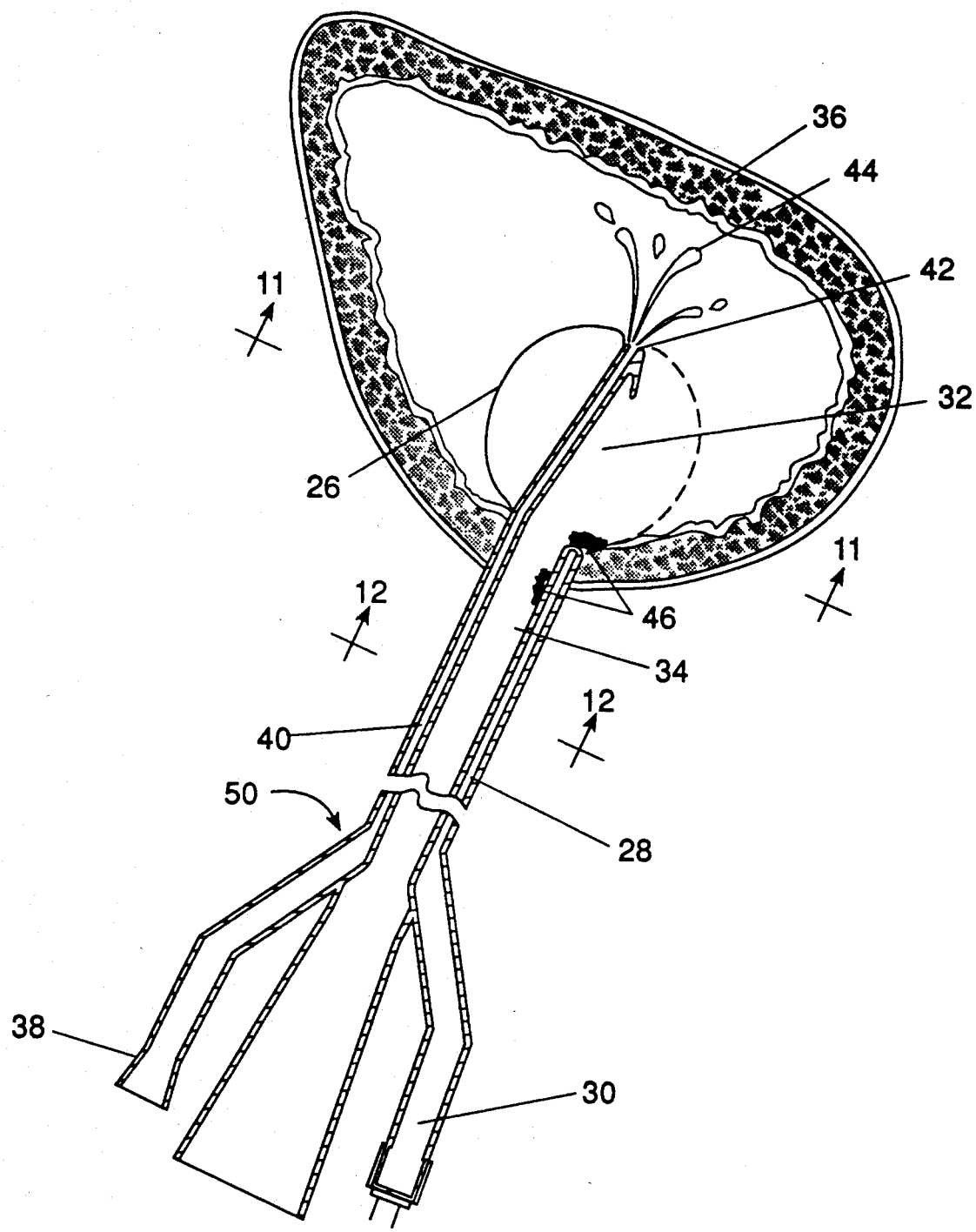
FIG. 9 is a cross sectional view of a bladder being irrigated with a different embodiment of the present invention in the form of a three-way catheter.

FIG. 9 shows a cross sectional view of another embodiment of the present invention in the form of a three-way irrigation catheter 50 being used to irrigate a bladder. The three-way catheter 50 differs from the two-way catheter 20 in having an additional channel 40 serving as a conduit for passage of irrigation fluid between an irrigation inlet 38 at the proximal end of the catheter and irrigation outlet 42 at the catheter's tip. As irrigation fluid is injected via inlet 38, it squirts out from outlet 42 and rinses the bladder cavity before draining out of drainage opening 32. Because opening 32 is larger than usual and situated at the lowest point in the bladder, it permits high speed and complete egress of fluid out of the bladder, washing away sediment, concretions, stones or blood clots which normally are resistant to removal using conventional three-way catheters. This is the fourth important advantage unique to the novel design of this catheter.

Figures 10, 11, 12:
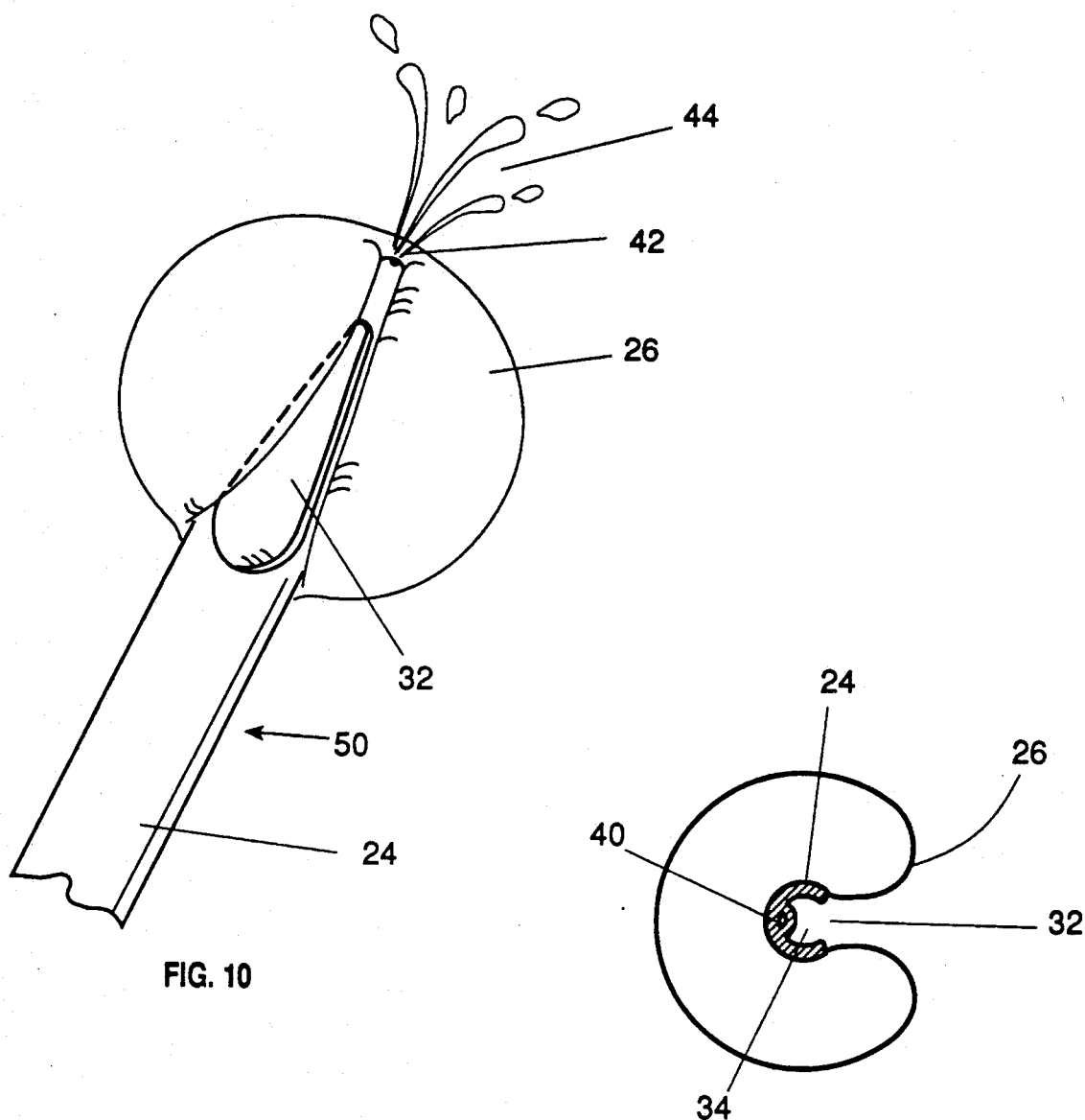
FIG. 10 is a perspective view of the distal end of the three-way catheter in FIG. 9 showing fluid being flushed out of the irrigation outlet.
FIG. 11 is a cross sectional view taken along line 11—11 of FIG. 9.
FIG. 12 is a cross sectional view taken along line 12—12 of FIG. 9.

FIG. 10 shows a perspective view of the distal end of the three-way catheter of FIG. 9, with irrigation fluid being ejected via irrigation outlet 42. As in the case of the two-way catheter, the catheter tip is visible only as a dimple upon inflation of the balloon whereupon a gully is formed over the drainage opening 32 by the two adjacent longitudinal edges of inflated balloon 26. These unique and novel features again result in a catheter that will not cause either catheter tip pressure injury or negative pressure injury.

FIG. 11 is a cross sectional view taken along line 11—11 in FIG. 9 showing the balloon partially circling the distal end of the catheter, the edges of the balloon being bonded or attached largely to the perimeter of the drainage opening 32. FIG. 12 is a like-view taken along line 12—12 of FIG. 9. The largest lumen within the catheter body is drainage lumen 34, followed by irrigation channel 40 and inflation channel 28.

SUMMARY, SCOPE AND RAMIFICATIONS

It is evident from the foregoing disclosure that the novel and unique designs of the catheter tip, the drainage opening, the partially circumscribing balloon and the resultant gully all create exceptionally functional catheters that not only completely drain the bladder, but also prevent the types of bladder injury and attendant discomfort and complications that have traditionally been associated with catheter therapy.

Even though many advantages and characteristics of the present invention have been described and set forth herein, together with details relating to the structure and function of the invention, the disclosure herein is illustrative only. It is anticipated by this invention that various modifications can be made as desired, some of which have been discussed in the preceding paragraphs. Other modifications include the deletion of the zero-tip feature in the two-way or three-way catheter, the addition of a second drainage opening such that the balloon becomes bipartate, and the use of specially reinforced material within or as the catheter tip.

Hence the present invention is not limited in its application to the details of the construction and to the arrangement of the different components set forth in this disclosure or illustrated in the drawings, as it is capable of other embodiment and of being practiced and carried out in various ways. It will be readily understood by those skilled in the art that changes may be made in form and detail, especially in matters of shape, size and arrangement of parts and aggregation of functional units, and in the use of functional equivalents and substitutes. Thus, for example, the catheter body may be made of latex and yet the balloon made of polyurethane because of the superior symmetrical inflation characteristics of polyurethane balloons. The optional reinforcement 52 for the catheter tip may be plastic or metal and can be in the form of a short strip or as a larger insert in the form of a conical cap with a cut-out to match drainage opening 32. Likewise, the use of this catheter is not limited to urology and can be effectively extended to other medical as well as non-medical applications. For example, this catheter would also be superior over conventional catheters in the drainage of the gall bladder or decompression of the bowel.

It is to be understood that the phraseology and terminology employed herein are for the purpose of description and should not be regarded as limiting. Those skilled in the art will appreciate that the conception of this invention may be readily utilized as a basis for the designing of other structures for carrying out the several purposes of the present invention, and to the full extent of the broad general meaning of the terms in which the claims are expressed. It is important therefore that the claims be regarded as including such equivalent approaches and constructions insofar as they do not depart from the spirit and scope of the present invention.

We claim:

1. A catheter, comprising:
a multi-lumen elongate structure having a main longitudinal lumen therein, a distal tapered end for insertion into a body cavity and a proximal end;
to said distal end or thereabouts of the elongate structure is attached at least one partially-circumscribing inflatable balloon having for inflation and deflation a passageway which connects and opens into said balloon and which terminates with a closable orifice or tubular duct at or near the proximal end;
at least one unobstructed opening near said distal end which opening extends through said structure to connect with said main lumen and allows passage of fluid between said main lumen and said body cavity, said opening being only partially circumscribed while being totally unenveloped by said inflatable balloon as further described below;
said inflatable balloon is made of highly elastic material and is attached at or near said distal end of said elongate structure with its distal boundary as close as appropriate to the tip of said tapered end such that upon normal inflation, the balloon expands not just partially circumscribingly around said tip but also distally to and away from the tip, which tip then becomes flush or recessed relative to the distal surface of the inflated balloon and in the distal portion of said elongate structure where the space leading to said opening is unobstructed and uncircumscribed by the inflated balloon, a gully leading to said opening is formed to facilitate drainage and to prevent negative pressure injury;
said inflatable balloon is attached at or near said distal end of said elongate structure such that upon inflation, it spans and envelopes an area extending from the tip region of the distal end of said elongate structure to terminate at a region that is peripheral to said unobstructed opening; and said terminating region, when measured from the distal end, is at a certain measured distance that is greater than that corresponding measurement and distance for the distal boundary of said opening, but less than or equal to that corresponding measurement and distance for the proximal boundary of said opening.

2. A catheter according to claim 1, wherein the distal portion at or near said opening is materially reinforced.

3. A catheter according to claim 2, wherein the distal portion at or near said opening is materially reinforced to prevent or reduce bending.

4. A catheter according to claim 3, wherein the distal portion at or near said opening is mechanically reinforced and buttressed by bonding with supporting props to prevent or reduce bending.

5. A catheter according to any one of the claims 1 through 4, wherein the opening is elongate longitudinally and extends towards the proximal end from an area within the balloon region or balloon segment to an area coextensive with the proximal periphery or boundary of said region or segment.

6. A catheter according to any one of the claims 1 through 4, wherein the opening is elongate longitudinally and extends and widens towards the proximal end from an area within the balloon region or balloon segment to an area coextensive with the proximal periphery or boundary of said region or segment.

7. A catheter according to any one of the claims 1 through 4, wherein the opening is elongate longitudinally and extends towards the proximal end from an area within the balloon region or balloon segment to an area outside of said region or segment.

8. A catheter according to any one of the claims 1 through 4, wherein the opening is elongate longitudinally and extends and widens towards the proximal end from an area within the balloon region or balloon segment to an area outside of said region or segment.

9. A catheter according to claim 1 wherein an additional channel or passageway for fluid flow is created which connects an opening or duct at or near the proximal region of the elongate structure to an opening at or near the distal end such that fluids may pass between said proximal opening or duct and said body cavity, via said channel or passageway, which is a passageway independent of and in addition to the passageway corresponding to the main lumen.

10. A catheter according to claim 9 wherein said opening at or near the distal end opens at the tapered tip of the elongate structure, or at a location immediately adjacent to said tapered tip.

11. A catheter according to claim 1 wherein two or more of the parts or components are of unitary construction.

12. A catheter according to claim 1 wherein said elongate structure is imprinted with one or more marks which are aligned in some manner relative to the drainage opening or some other distal structural feature of the catheter so as to provide an indication of orientation, degree of rotation or torsion, and depth of insertion of the catheter.

13. A catheter according to claim 1 wherein said elongate structure is imprinted with one or more graudated longitudinal marker lines which is aligned in some manner relative to the drainage opening or some other distal structural feature of the catheter so as to provide an indication of orientation, degree of rotation or torsion, and depth of insertion of the catheter.

14. A catheter according to claim 12 or claim 13 wherein said markings are of high-contrast ink or color.

15. A catheter according to claim 12 wherein said markings are radiopaque.

16. A catheter, comprising:
a multi-lumen elongate structure having a main longitudinal lumen therein, a distal tapered end for insertion into a body cavity and a proximal end;
to said distal end or thereabouts of the elongate structure is attached at least one partially-circumscribing inflatable balloon having for inflation and deflation a passageway which connects and opens into said balloon and which terminates with a closable orifice or tubular duct at or near the proximal end;
at least one unobstructed opening near said distal end which opening extends through said structure to connect with said main lumen and allows passage of fluid between said main lumen and said body cavity, said opening being only partially circumscribed and unobstructed by said inflatable balloon; and wherein said inflatable balloon is made of highly elastic material and is attached at or near said distal end of said elongate structure with its distal boundary as close as appropriate to the tip of said tapered end such that upon normal inflation, the balloon expands not just partially circumscribingly around said tip but also axially with respect to said tip, which tip then becomes substantially flush with the distal surface of the inflated balloon and in the distal portion of said elongate structure where the space leading to said opening is unobstructed and uncircumscribed by the inflated balloon, a gully leading to said opening is formed to facilitate drainage and to prevent negative pressure injury.

17. A catheter according to claim 16, wherein the distal portion at or near said opening is materially reinforced.

18. A catheter according to claim 16, wherein the opening is elongate longitudinally and extends towards the proximal end from an area within the balloon region or balloon segment to an area coextensive with the proximal periphery or boundary of said region or segment.

19. A catheter according to claim 16, wherein an additional channel or passageway for fluid flow is created which connects an opening or duct at or near the proximal region of the elongate structure to an opening at or near the distal end such that fluids may pass between said proximal opening or duct and said body cavity, via said channel or passageway, which is a passageway independent of and in addition to the passageway corresponding to the main lumen.

20. A catheter according to claim 16, wherein said elongate structure is imprinted with one or more marks which are aligned in some manner relative to the drainage opening or some other distal structure feature of the catheter so as to provide an indication of orientation, degree of rotation or torsion, and depth of insertion of the catheter.

21. A catheter, comprising:
a multi-lumen elongate structure having a main longitudinal lumen therein, a distal tapered end for insertion into a body cavity and a proximal end;
to said distal end or thereabouts of the elongate structure is attached at least one partially-circumscribing inflatable balloon having for inflation and deflation a passageway which connects and opens into said balloon and which terminates with a closable orifice or tubular duct at or near the proximal end;
at least one unobstructed opening near said distal end which opening extends through said structure to connect with said main lumen and allows passage of fluid between said main lumen and said body cavity, said opening being only partially circumscribed and unobstructed by said inflatable balloon; and wherein said inflatable balloon is attached at or near said distal end of said elongate structure such that upon inflation, it spans and envelopes an area extending from the tip region of the distal end of said elongate structure to terminate at a region that is peripheral to said unobstructed opening, and wherein part of said unobstructed opening is within the longitudinal span of the balloon.

22. A catheter according to claim 21, wherein said terminating region, when measured from the distal end, is at a certain measured distance that is greater than that corresponding measurement and distance for the distal boundary of said opening, but substantially equal to that corresponding measurement and distance for the proximal boundary of said opening.

23. A catheter according to claim 21, wherein the distal portion at or near said opening is materially reinforced.

24. A catheter according to claim 21, wherein the opening is elongate longitudinally and extends towards the proximal end from an area within the balloon region or balloon segment to an area coextensive with the proximal periphery or boundary of said region or segment.

25. A catheter according to claim 21, wherein an additional channel or passageway for fluid flow is created which connects an opening or duct at or near the proximal region of the elongate structure to an opening at or near the distal end such that fluids may pass between said proximal opening or duct and said body cavity, via said channel or passageway, which is passageway independent of and in addition to the passageway corresponding to the main lumen.

26. A catheter according to claim 21, wherein said elongate structure is imprinted with one or more marks which are aligned in some manner relative to the drainage opening or some other distal structure feature of the catheter so as to provide an indication of orientation, degree of rotation or torsion, and depth of insertion of the catheter.

* * * * *